(12) United States Patent
Fiedler et al.

(10) Patent No.: US 10,973,661 B2
(45) Date of Patent: Apr. 13, 2021

(54) ALIGNMENT ANGLE SENSOR SYSTEMS FOR LIMB PROSTHESES

(71) Applicant: University of Pittsburgh—Of the Commonwealth System of Higher Education, Pittsburgh, PA (US)

(72) Inventors: Goeran Fiedler, Pittsburgh, PA (US); Jonathan Stephen Akins, Haddonfield, NJ (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 428 days.

(21) Appl. No.: 15/761,766

(22) PCT Filed: Sep. 29, 2016

(86) PCT No.: PCT/US2016/054510
§ 371 (c)(1),
(2) Date: Mar. 20, 2018

(87) PCT Pub. No.: WO2017/059115
PCT Pub. Date: Apr. 6, 2017

(65) Prior Publication Data
US 2020/0237532 A1    Jul. 30, 2020

Related U.S. Application Data

(60) Provisional application No. 62/235,766, filed on Oct. 1, 2015.

(51) Int. Cl.
*A61F 2/76*    (2006.01)
*A61F 2/62*    (2006.01)
(Continued)

(52) U.S. Cl.
CPC .............. *A61F 2/76* (2013.01); *A61F 2/60* (2013.01); *G01B 7/30* (2013.01);
(Continued)

(58) Field of Classification Search
None
See application file for complete search history.

(56) References Cited

U.S. PATENT DOCUMENTS

| 4,661,773 A | 4/1987 | Kawakita et al. |
| 4,986,280 A | 1/1991 | Marcus et al. |

(Continued)

FOREIGN PATENT DOCUMENTS

| WO | WO 2005/018453 | 3/2005 |
| WO | WO 2010/005473 | 1/2010 |
| WO | WO 2011/026086 | 3/2011 |

OTHER PUBLICATIONS

International Search Report and Written Opinion for related International Application No. PCT/US2016/054510, dated Dec. 20, 2016, 14 pages.

(Continued)

*Primary Examiner* — David H Willse
(74) *Attorney, Agent, or Firm* — Klarquist Sparkman, LLP

(57) ABSTRACT

Disclosed herein are systems and methods for determining alignment angles between a first prosthetic component and a second prosthetic component that are joinable together in a fixed orientation relative to each other, wherein the fixed orientation includes a first angle and optionally also a second angle that are perpendicular to each other, and wherein the first and/or second angles are selectable from a range of angles to provide a desired fixed orientation between the two prosthetic components. The system includes a magnet fixedly coupled to the first prosthetic component and one or (Continued)

more magnetic intensity sensors configured to be coupled to the second prosthetic component in a fixed orientation relative to the second prosthetic component such that the sensors are operable to sense a magnetic field of the magnet and produce an output signal in response to the strength of the sensed magnetic field. The system can include a processor operable to receive the output signals from the sensors and determine the first and/or second angles.

17 Claims, 9 Drawing Sheets

(51) Int. Cl.
    *A61F 2/70*     (2006.01)
    *A61F 2/60*     (2006.01)
    *G01B 7/30*     (2006.01)
    *A61F 2/66*     (2006.01)
    *A61F 2/68*     (2006.01)
    *A61F 2/50*     (2006.01)
    *A61F 2/30*     (2006.01)

(52) U.S. Cl.
    CPC ............... *A61F 2002/30538* (2013.01); *A61F 2002/5018* (2013.01); *A61F 2002/5083* (2013.01); *A61F 2002/5096* (2013.01); *A61F 2002/6614* (2013.01); *A61F 2002/6863* (2013.01); *A61F 2002/7625* (2013.01); *A61F 2210/009* (2013.01); *A61F 2250/0006* (2013.01)

(56) References Cited

U.S. PATENT DOCUMENTS

| | | |
|---|---|---|
| 5,969,520 A | 10/1999 | Schottler |
| 6,050,962 A | 4/2000 | Kramer et al. |
| 6,847,205 B2 | 1/2005 | Puech |
| 7,922,773 B1 | 4/2011 | Kuiken |
| 8,500,823 B2 | 8/2013 | Herr et al. |
| 2003/0220701 A1 | 11/2003 | Steinbarger et al. |
| 2010/0201351 A1 | 8/2010 | Clymer |
| 2013/0310979 A1 | 11/2013 | Herr et al. |
| 2015/0105782 A1 | 4/2015 | D'Lima et al. |
| 2017/0128236 A1* | 5/2017 | Meyer .................. A61F 2/6607 |

OTHER PUBLICATIONS

Search Report for related European Application No. 16852621.8, dated Oct. 17, 2019, 13 pages.

* cited by examiner

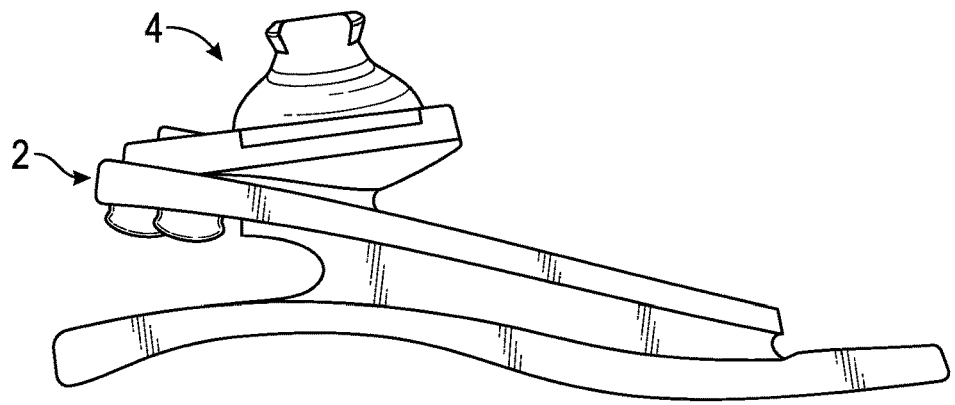
FIG. 1A [PRIOR ART]
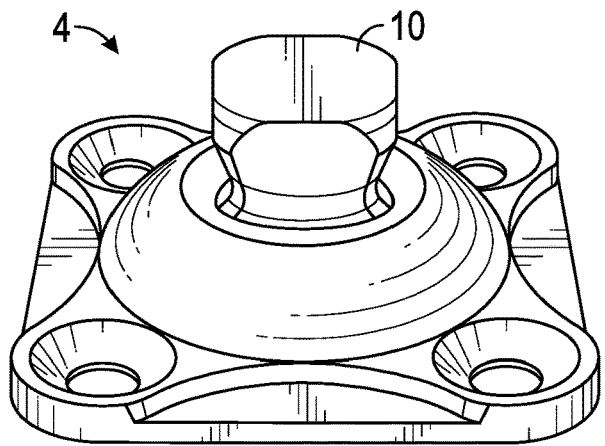
FIG. 1B [PRIOR ART]
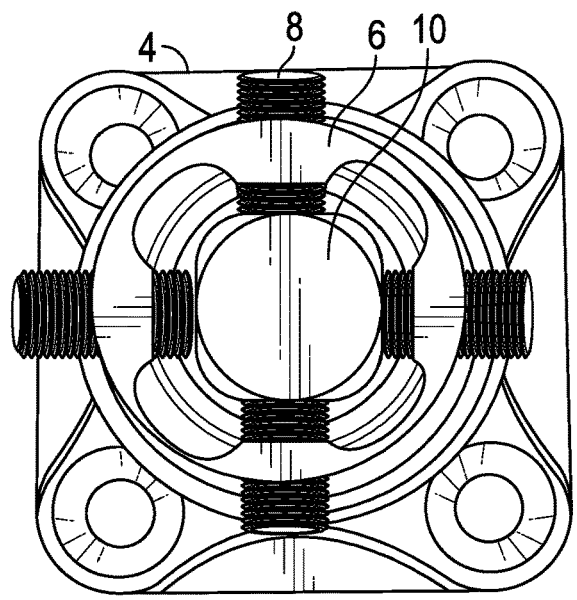
FIG. 1C [PRIOR ART]

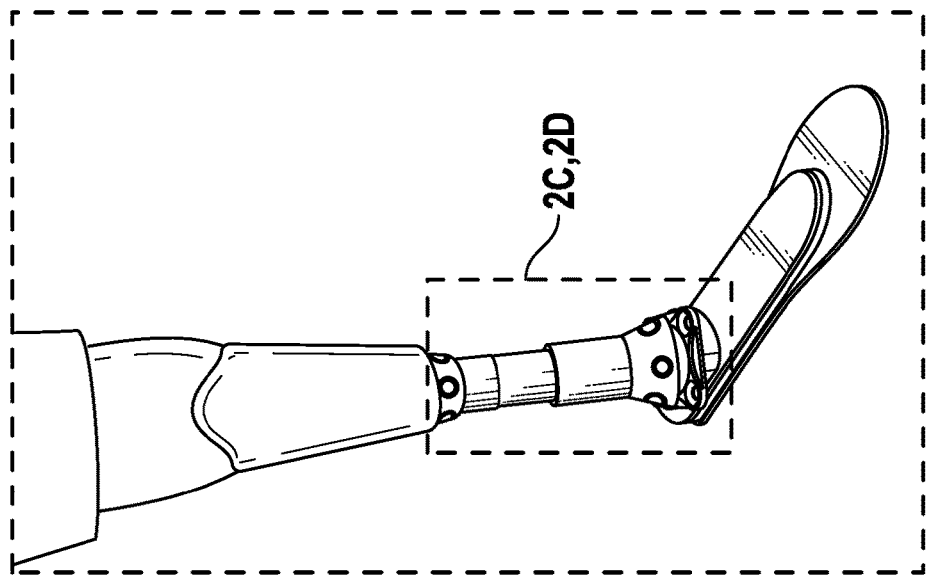
FIG. 2B [PRIOR ART]
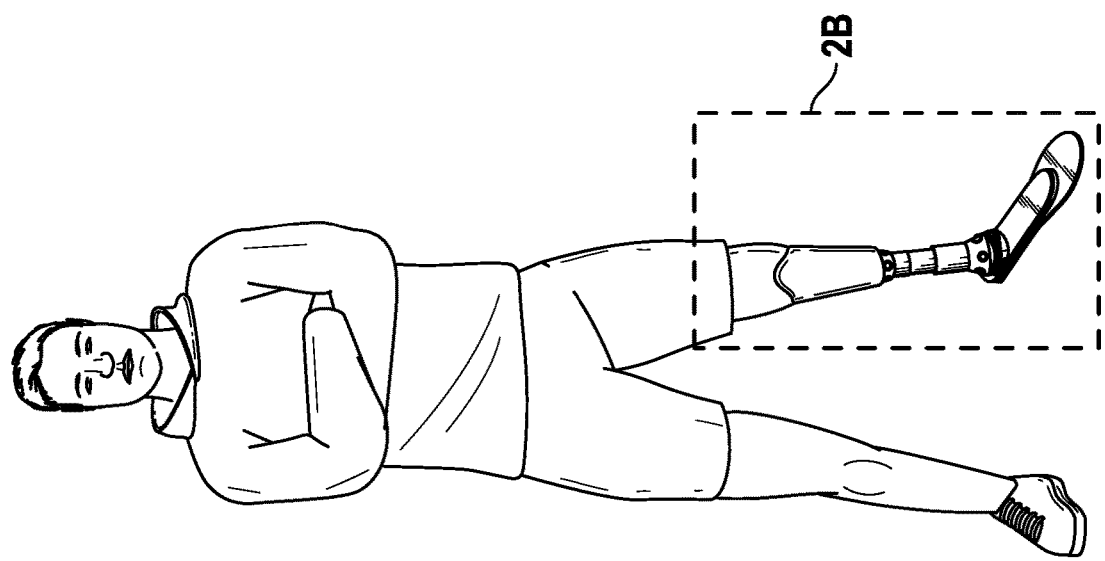
FIG. 2A [PRIOR ART]

$L_1$

ALIGNMENT ANGLE SENSOR SYSTEMS FOR LIMB PROSTHESES

CROSS-REFERENCE TO RELATED APPLICATIONS

This application is the U.S. National Stage of International Application No. PCT/US2016/054510, filed Sep. 29, 2016, which claims the benefit of U.S. provisional patent-application No. 62/235,766, filed Oct. 1, 2015, which is incorporated by reference herein in its entirety.

FIELD

This application is related to devices, systems, and methods for determining alignment angles for limb prostheses.

BACKGROUND

In 2005, there were an estimated 1.04 million people living in the US with lower limb loss. By 2050 that number is expected to increase significantly due to increased rates of dysvascular disease, diabetes, trauma and cancer. Because of this increased rate of lower limb loss, more people will need lower limb prosthetics and more visits to practitioners for prosthetic alignment will occur. Such alignment is necessary to prevent patient discomfort, improper body alignment and poor energy expenditure.

Adjustments to lower limb prosthetics are typically made by changing the bi-planar alignment angles of pyramid adaptors. Typically made out of titanium, aluminum or stainless steel, pyramid adaptors are connected to patients' prosthetic knee joints, prosthesis sockets or spacers (FIGS. 1A and 1B, showing conventional pyramid adapter 4 connected to a prosthetic foot). Pyramid adaptors can be fitted together with pyramid receptors on adjacent parts that contain four screws (FIG. 1C, showing a top view of a pylon/receptor 6 secured to the adaptor 4 via set screws 8 in contact with a central post 10 of the pyramid adaptor 4).

Within a lower limb prosthetic (see, e.g., FIGS. 2A, 2B, 2C, and 2D), alignment is based on the adjustment of these four screws 8A, 8B until the end surfaces of the pylon 6 are resting on the spherical domes of the pyramid adaptors 4A, 4B at the appropriate bi-planar angles, then the screws 8A, 8B can be tightened against the central posts 10A, 10B to fix the position. A prosthesis's pyramid adaptors should remain parallel with one another when alignment adjustments are made (FIGS. 2C and 2D). To date, there is no standardized way to quantify alignment angles. Practitioners estimate or count screw rotations to measure their adjustment. The lack of clear, repeatable alignment angles limits the efficiency of clinical practice and research protocols. This is particularly important for evidence based practice and proper documentation of care interventions.

SUMMARY

Disclosed herein are systems and methods for determining alignment angles between a first prosthetic component and a second prosthetic component that are joinable together in a fixed orientation relative to each other, wherein the fixed orientation includes a first angle and a second angle that are perpendicular to each other, and wherein the first and second angles are selectable from a range of angles to provide a desired fixed orientation between the two prosthetic components. The system includes a magnet fixedly coupled to the first prosthetic component and one or more magnetic intensity sensors for sensing the magnetic field of the magnet (e.g., magnetometers and/or Hall effect sensors), the sensors configured to be coupled to the second prosthetic component in a fixed orientation relative to the second prosthetic component, such that the sensors are operable to sense/measure the magnetic field of the magnet and produce an output signal in response to the intensity/magnitude of the magnetic field. The system can include a processor operable to receive the output signal from the sensors and determine the first and/or second angles.

The system can include a device or system to temporarily secure the magnetic intensity sensors to the second prosthetic component. For example, a removable sleeve or wrap that includes the magnetic intensity sensors can be configured to be secured around the second prosthetic component temporarily to determine the orientation between the two prosthetic devices, and then removed after the angles are selected and fixed. The sleeve or wrap can also include the processors, a voltmeter, and/or a power supply. In other embodiments, a hand-actuated clamp carrying the magnetic intensity sensors can be temporarily attached to the second prosthetic component during angle alignment, then removed once the angle is fixed. Variations of these sensor-carrying devices can also be configured to be left attached to the second prosthetic component during future use of the prosthetic (e.g., they can be made lightweight, low profile, durable, waterproof, etc.).

The processor can be in communication with a display to show the determined angles in real time. The processor can also be in communication with a separate computer or handheld device to allow the measurements to be stored to internal memory of the device and/or sent securely to a centralized database. Once desired angles are achieved, set screws or other fasteners can be tightened to fix the angles. The display can be integrated with other components, or remote, or on a computer screen, or in any other format allowing a user to read the measured angles and set the prosthetic at a desired orientation.

The first prosthetic component can include a pyramid adapter and the magnet can be fixed to the pyramid adapter, can be positioned inside the pyramid adapter, can be positioned adjacent to the pyramid adapter, or can be a part of the pyramid adapter. The magnet can be a spherical magnet, a disk-shaped magnet, or various other shapes. In some cases, more than one magnet can be included.

The first and second prosthetic components can be lower limb prosthetic components, or can be other anatomical prosthetic components.

The foregoing and other objects, features, and advantages of the disclosed technology will become more apparent from the following detailed description, which proceeds with reference to the accompanying figures.

BRIEF DESCRIPTION OF THE DRAWINGS

FIG. 1A is a side view of a prosthetic foot including an adapter.

FIG. 1B is a perspective view of an exemplary prosthetic adapter including a spherical surface and a pyramid adapter.

FIG. 1C is a top view of the prosthetic adapter of FIG. 1B with a lower portion of a pylon secured to it using four set screws.

FIGS. 2A and 2B illustrate the anatomical location of an exemplary lower limb prosthesis.

DETAILED DESCRIPTION

Figure 2C:
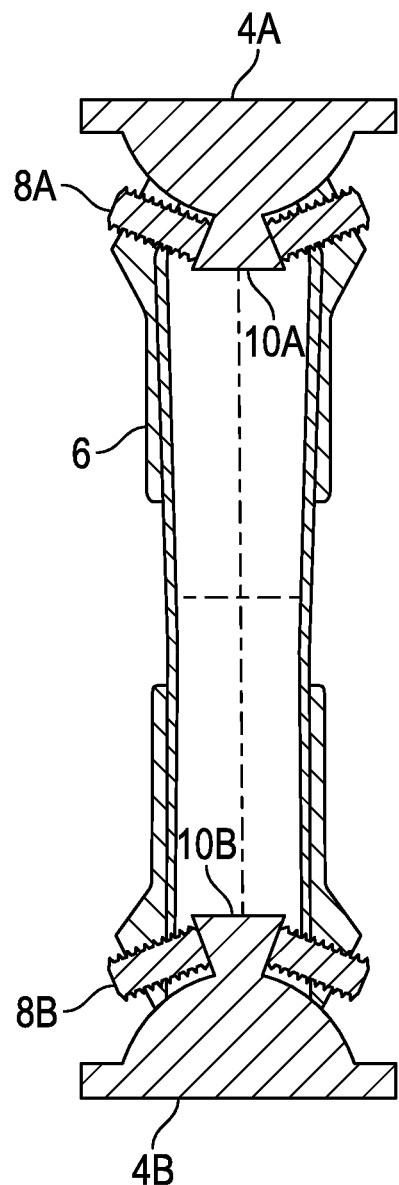
FIGS. 2C and 2D illustrate the adjustment of an exemplary modular pyramid adaptor system for a lower limb prosthesis.
Figure 2D:
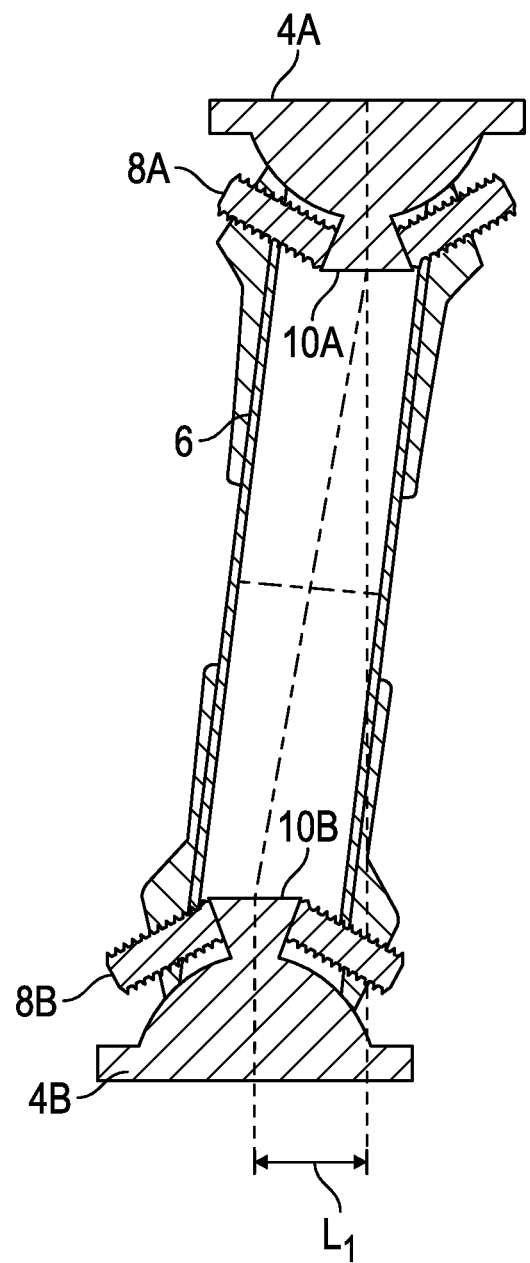

Magnetic intensity sensors, such as magnetometers and Hall effect sensors, can output voltages in response to sensed magnetic field strength. If placed near a magnet, the position of a sensor relative to that magnet can be determined based on the sensor's output voltage. For this reason, sensors can be used as proximity sensors to measure a distance from a magnet to the sensor and the orientations of the sensor with respect to the magnet. The magnetic field intensity is greatest when the magnet is touching the sensor and decreases exponentially as the magnet moves away. In an exemplary embodiment described herein, an analog gauge Digi-Key Electronics MLX90215 Hall Effect Sensor can be used to provide a gradual transition between voltages. Magnetometers, potentiometers and/or accelerometers can also be used in the disclosed systems for determining angles and/or positions. Potentiometer or potentiometer arrays, for example, (like an analog joystick) may provide accurate rotation to angle conversions. Accelerometers can similarly provide accurate angle and position measurements. Any combination of or one or more magnetometers, Hall effect sensors, accelerometers, potentiometers, other magnetic intensity, and/or other types of sensors can be used in the technology disclosed herein.

One, two, three, four, or more sensors can be attached to the outside or inside of a pylon, or to other devices that are coupled to the pylon, such as by including the one or more sensors in a clamp or in a sleeve or wrap that is positioned around the pylon and/or adapter. The one or more sensors may be powered externally, such that the only permanent internal component is a small magnet. In some embodiments, one or more sensors can be powered by on-board batteries or other power sources that remain with the prosthetics while in use. In some embodiments, any combination of the sensors, power sources, processors, and/or displays of the disclosed systems can remain coupled to the prosthetics permanently and/or while the user performs normal day-to-day activities with the prostheses.

Developing suitable alignment angle measurement systems using magnetic intensity sensors can include, but is not limited to, 1) determining the most desirable sensor positions by investigating the relationship between sensor placement and magnetic field strength at various alignment angles; 2) determining conversions between sensor output voltage (or other output signal) and the linear distances between the magnet and the sensors; and 3) developing a functional sensor system for angle measurement (e.g., bi-planar X and Y angles) and communicating the determined angles to a user.

In an exemplary development process, to determine suitable magnetic intensity sensor placements relative to the magnet and prostheses, the magnetic field strength of a magnet fixed to the top of pyramid adapter relative to outside of the pylon was measured as the pylon moved along the pyramid adaptor from 00 to 18°. This angle range mimicked the conventional 18° adjustment capability of an exemplary pyramid adaptor being used (the disclosed technology can be used to determine angles having any range, and is not limited a 0-18 degree range).

A testing fixture consisted of two pyramid adaptors, each attached to two rigid bases planks, and connected with a pylon. A magnet was secured on the lower pyramid adaptor and a Gaussmeter probe was attached to the outside of the pylon to measure the magnet's strength. A digital protractor was attached to the upper plank to gauge angular motion. While the bottom plank and adaptor remained stationary, the pylon and digital protractor moved from 00 to 18° along the lower pyramid adaptor. Data was collected in two testing fixture orientations, parallel and perpendicular, to account for the X and Y placement of sensors (see X and Y directions in FIG. 3). For each orientation, the Gaussmeter probe was attached to four different sections of the magnet to measure the magnetic field strength every 0.50. The Gaussmeter probe recognized the strongest magnetic field when the vertical position of the probe was around the center section of the magnet.

An exemplary disk-shaped neodymium rare-earth magnet was used in one experiment. For the disk-shaped magnet, the strongest magnetic field readings occurred in front of the magnet's North pole. Measurements in the X direction were stronger than those in the Y direction because the probe was directly in front of the North pole when testing in the X direction.

Figure 3:
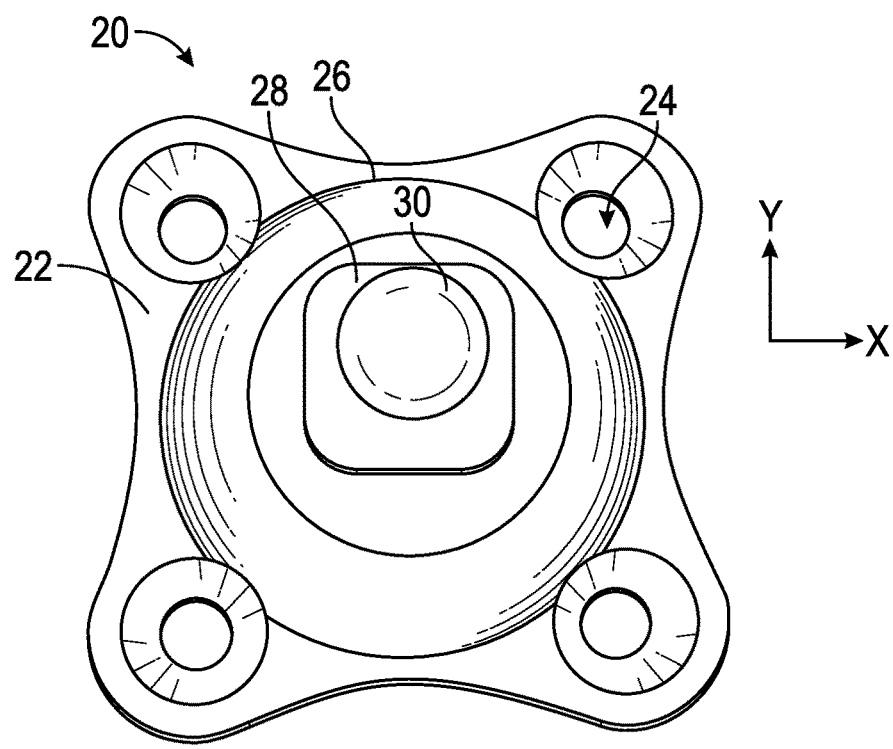
FIG. 3 is a top view of an exemplary pyramid adapter with a spherical magnet on its upper aspect, showing the X and Y axes along which angles between joint prosthetic components can be measured.
Figure 4:
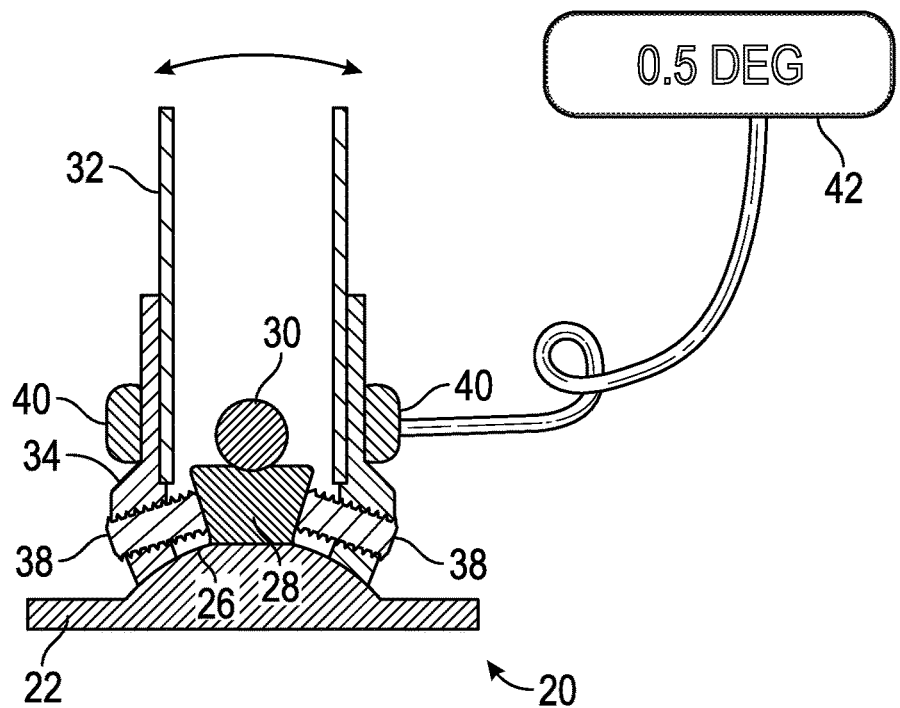
FIG. 4 is a cross-sectional view of an exemplary system including an upper prosthetic pylon secured to a lower pyramid adapter with a magnet, as shown in FIG. 3, with magnetic intensity sensors coupled to the upper prosthetic pylon to measure the magnetic field, and a display showing an angle as determined based on signals from the sensors.
Figure 5A:
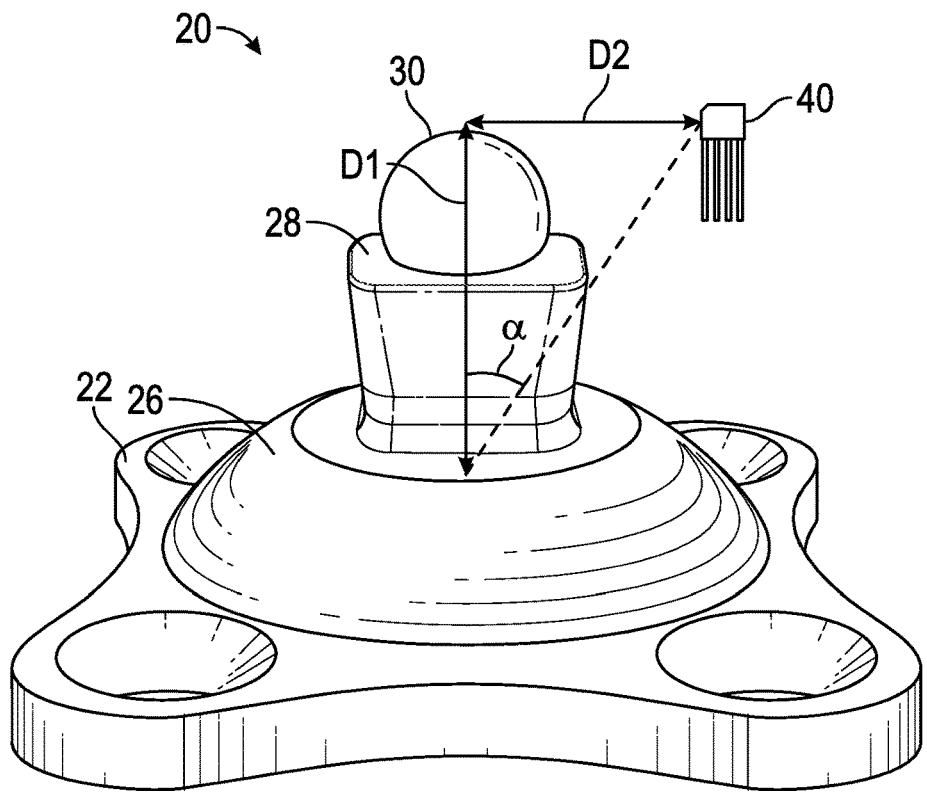
FIG. 5A shows a pyramid adapter with an attached spherical magnet and an adjacent magnetic intensity sensor, and illustrates parameters that can be used to calculate the angle of an attached prosthetic pylon using the disclosed technology.

In other embodiments, as shown in FIGS. 3, 4, and 5A, a substantially sphere-shaped magnet can be used rather than a disk magnet. The sphere magnet provides more uniform magnetic field lines for both the X and Y directions since only the North pole is exposed (in the tested configuration).

In some configurations, a disk magnet exposes both the North and South poles and the Y sensor can fall in between them. The X and Y directions can correspond to perpendicular anatomical planes or directions, such as the frontal and sagittal planes.

Figure 12:
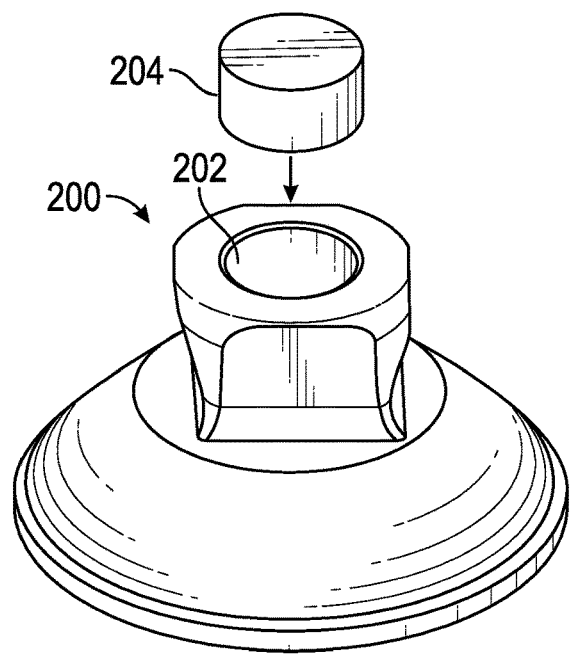
FIG. 12 shows an exemplary pyramid adapter having a recess in the top of its central post that is configured to receive a magnet.

As shown in FIGS. 3, 4, and 5A, the adapter 20 comprises a base 22 that can be secured to a prosthetic device (e.g., a foot) via holes 24, a spherical surface 26 for contacting the bottom of the opposing prosthetic device (e.g., a pylon), a central post 28 that is configured to contact set screws of the opposing prosthetic device, and a substantially spherical magnet 30 attached to the top of the central post. FIG. 12 shows an alternative adapter 200 wherein a magnet 204 is mounted in a recess 202 in the top of the central post. The magnet can comprise a neodymium rare-earth magnet, as just one example. The magnet can be permanently or removably attached to the adapter, such as by welding, adhesive, screw, clamp, other mechanical fasteners, etc. Any shape of magnet can be used in the disclosed technology, with the spherical magnets being just one preferred shape.

FIG. 4 shows the adapter 20 secured to an upper prosthetic pylon that includes a shank 32 and a lower connector 34 in contact with the spherical surface 26 while set screws 38 contact the central post 28 to hold the joint fixed. The magnet 30 is positioned inside the pylon 32. Magnetic intensity sensors 40 are shown positioned outside the pylon at the level of the magnet, and electrically coupled to a display 42 that displays the current angle as determined by a processor based on output signals from the sensors 40. Two sensors are shown in FIG. 4 on opposing sides of the pylon, though any number of sensors can be included in any circumferential arrangement around the pylon. The sensors can also be positioned at differing vertical positions in some embodiments.

Figure 5B:
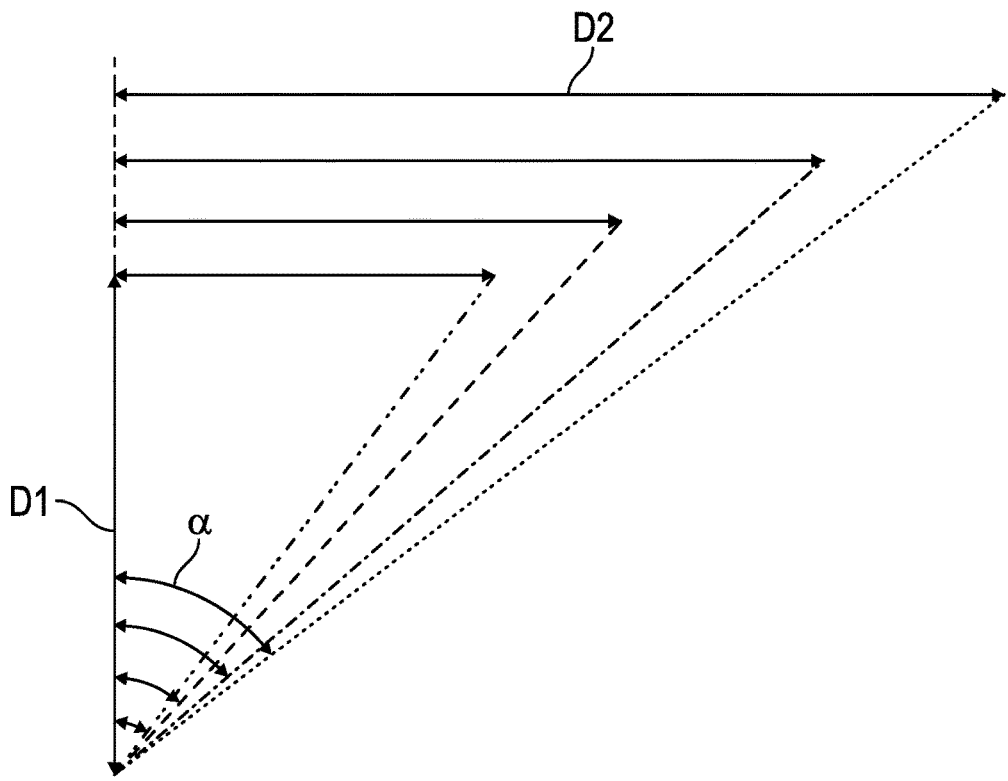
FIG. 5B provides an illustration for determining the angle between a pyramid adapter and attached prosthetic pylon using the disclosed technology.

Since magnetic intensity sensors can respond with output voltages in the presence of a magnetic field, a conversion between voltage and distance can be used to determine the angle of each sensor relative to the base of the pyramid portion of the pyramid adaptor (e.g., using trigonometry). With reference to FIGS. 5A and 5B, the linear distance D2 between the magnet 30 and a sensor 40 and a fixed distance D from the top of the magnet to the base of the pyramid portion of the pyramid adaptor (or alternatively the center of curvature of the spherical portion 26), the angle alpha of the sensor can be determined using trigonometry.

Figure 6:
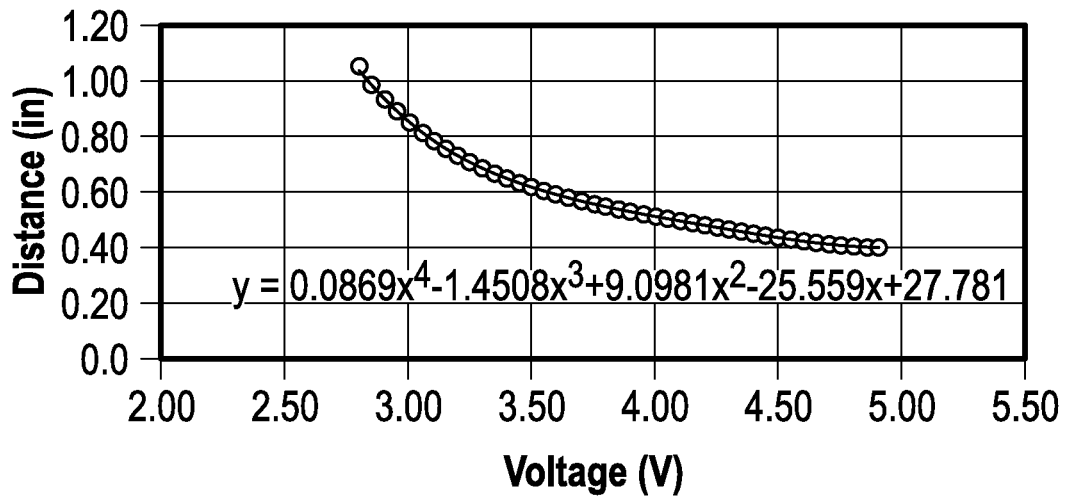
FIG. 6 is a graph showing a relationship between the magnetic intensity sensor voltage and the distance between the magnet and the magnetic intensity sensor when a prosthetic pylon is not attached to the pyramid adapter.
Figure 7:
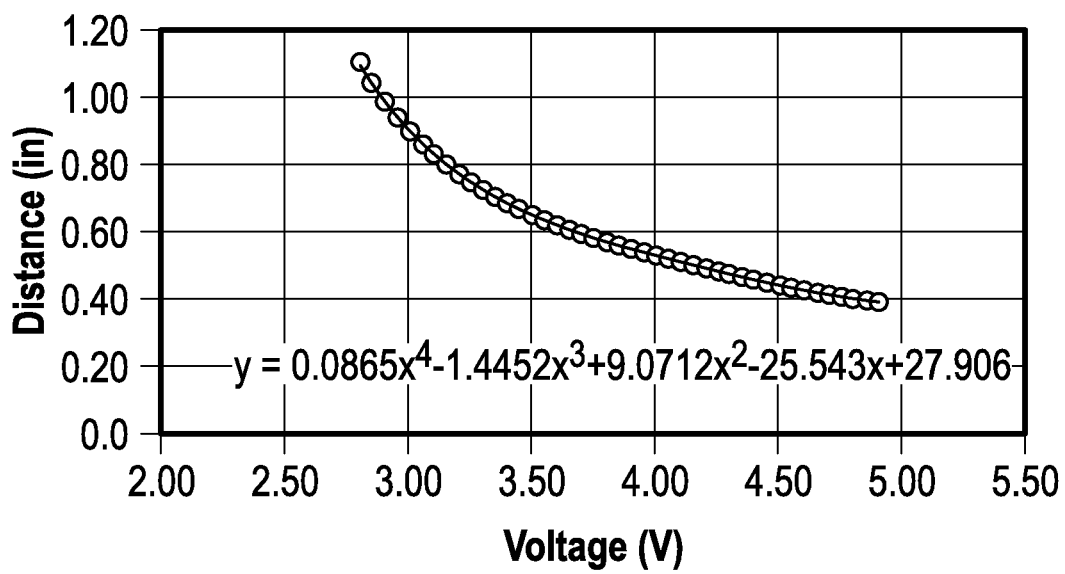
FIG. 7 is a graph showing a relationship between the magnetic intensity sensor voltage output and the distance between the magnet and the sensor when a prosthetic pylon is attached to the pyramid adapter and the magnet is inside of the pylon.

An exemplary voltage to distance conversion was determined using an experimental lathe set-up (see provisional application No. 62/235,766 filed Oct. 1, 2015, which is incorporated by referenced herein it its entirety). The experimental lathe set-up included a neodymium rare earth magnet attached to an aluminum bar in a stationary chuck of a lathe, a Hall effect sensor placed directly in front of the magnet on the tool mount to sense the magnetic field as a lathe was rotated to control linear movement of the Hall effect sensor relative to the magnet in the Z direction, a circuit board and Arduino powering the sensor set-up, and a Multimeter display of the Hall effect sensor's voltage. The spherical magnet was placed on an aluminum bar in a stationary chuck of the lathe and a Hall effect sensor set-up was placed directly in front of the magnet on the tool mount. Voltages were displayed on a multimeter. The Hall effect sensor moved linearly in the Z direction away from the magnet and distances were recorded every 0.05 Volts. Three trials were run for the sensors without the pylon and two trials were run with the pylon. Resulting measurements without the pylon were averaged and plotted (FIG. 6). Measurements from two additional trials were averaged and plotted with the Hall effect sensor on the pylon to verify that the pylon would not alter the data collected (FIG. 7).

Though the differential form of Gauss's Law can be used for the range and purpose of this technology, a simpler fourth order polynomial approximation is sufficient. Each of the data plots were then fitted with trendlines. The lines of best fit were fourth order polynomial trendlines. To convert voltages to distance, their trendline equation was used:

$$y=0.087x^4-1.45x^3+9.08x^2-25.55x+27.85 \quad (1)$$

where y is the resulting distance (inches) between the Hall effect sensor and the magnet and x is the voltage (volts) of the Hall Effect Sensor in this equation.

This y distance can then be used in the trigonometric equation modeled from FIGS. 5A and 5B:

$$A = \tan^{-1}\left(\frac{D1}{Y}\right) \quad (2)$$

where A is the angle of interest of the Hall effect sensor relative to the bottom of the pyramid portion of the pyramid adapter, and D is a known vertical distance from the top of the magnet to the bottom of the pyramid portion.

$R^2$ values for the data sets both with and without the pylon indicated strong correlation with the fitted curve. The $R^2$ for the dataset with the pylon was 0.9995 with a root mean squared error of 0.49% and that without the pylon was 0.9993 with root mean squared error of 0.53%.

In another example, data were collected using a three-dimensional or tri-axis magnetometer (e.g., a digital compass) and an accelerometer. The set-up comprised of a rare-Earth magnet held in place on a standard pyramid adaptor and the sensors attached to a pylon. The adaptor was clamped down for stability, and the two sensors were positioned along the frontal and sagittal planes of an aluminum pylon respectively, which was connected to the pyramid adaptor. The sensors were connected to an Arduino Uno microcontroller for collecting data. Data were collected from the pylon as its position was adjusted by half-screw-turns from the −y to +y and back to the −y position with respect to the frontal sensors. Turns were done at 15 s intervals to allow for more obvious data point readings. The same was done along the z axis. The best results were obtainable from the sensor that moved parallel to the axis of movement. Acceleration in all three directions was processed and plotted. Trends were noted and compared to similarly processed magnetometer data of magnetic intensity. These data were used to create a meaningful angle measurement using arctan 2 of the changing measurement (z axis or y axis) via the following equation: $\alpha_y$=a tan(y,√(x²+z²)). Data from the accelerometer provided an easy and consistent degree from the ground, and magnetometer data were given an adjustment factor to create a similar curve. A degree of hysteresis was identified when plotting accelerometer versus magnetometer angles. To reduce the hysteresis, distances between the sensor and the pylon were tested from 0.4-1.5 cm at 1 mm increments. The optimal distance was found to be 0.5 cm separation, as visually determined via direct comparisons of trials. At the optimal distance, there was a trending correlation between accelerometer and magnetometer data, translating to measurements that correspond to real angles, related by the equation:

$$y=1.5*10^{-5}x^3-0.00023x^2+0.077175x-5.8603 \quad (3).$$

It was determined that an example procedure for successful device use could entail the user calibrating the device at zero degrees according to the accelerometer, which would prompt the device to base all further magnetometer measurements off of this point. The data gathered as well as the successful trend of the data relationship strongly indicates that accurate readings of prosthesis angle can be accomplished with the tested device.

Exemplary Devices and Systems

Figure 8:
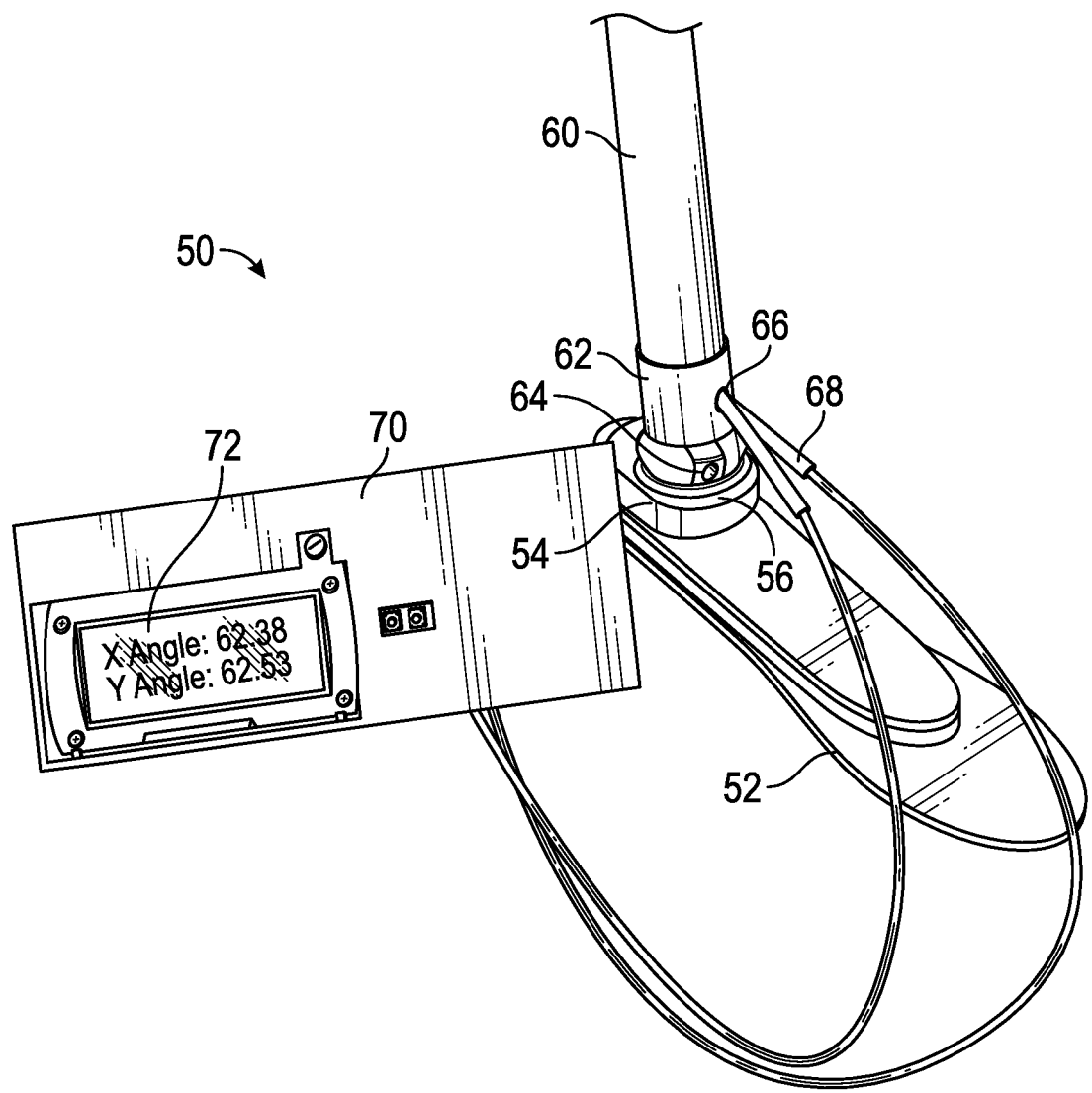
FIG. 8 shows an exemplary prototype magnetic intensity sensors system that includes two magnetic intensity sensors and a handheld module with a digital display showing the determined X and Y angles.

Various working prototype devices were created to measure the bi-planar alignment angles of pyramid adaptors using the herein described technology. FIG. 8 shows one exemplary prototype sensor system that was built using a circuit board that was programmed and powered with the Arduino UNO. In this embodiment, a magnet is attached to the top of the pyramid adaptor 56. Two magnetic intensity sensors were held in place on the exterior of the pylon; one in the X direction and another in the Y direction. The sensors were connected via wires to a handheld case that houses the power supply, zero buttons, and LCD display. The LCD board can provide users with a digital readout of the X and Y alignment angles (as shown in FIG. 8) and/or other data. The two calibration buttons can be used to zero and reset the angles.

The system 50 shown in FIG. 8 includes a prosthetic foot/shoe 52 with attachment portion 54, pyramid adapter 56 attached to the foot portion, pylon 60 secured to the pyramid adapter 56 via set screws 64, with a magnet of the pyramid adapter positioned inside the pylon, sensors 66 placed on the outer side of the pylon via a sleeve or wrap 62 positioned around the lower end of the pylon, wires 68 extending from the sensors to a processing unit 70, and a display 72 coupled to the unit 70 to show calculated X and Y angle measurements. A sleeve/clamp for holding the sensors relative to the pylon 60 is not shown in FIG. 8.

In some embodiments, one or two or more Hall effect sensors, magnetometers, accelerometers, potentiometers, and/or other types of sensors can be carried by a sleeve or wrap or clamp, etc., that is attachable around the pylon and/or other prosthetic device adjacent to the magnet. The sleeve or wrap or clamp, etc., can be part of a temporary sensor attachment system that can be temporarily positioned on the prosthetic with the sensors in a desired orientation relative to the magnet, angle adjustments/settings can be performed using a display to determine a desired X and Y angle, and then the sleeve or wrap can be removed. In the case of a sleeve or wrap, the temporary sensor attachment system can comprise a fabric material or other flexible material. The temporary sensor attachment system can also include a power source and/or be attached to a power source, such as with a cord and wall plug. The temporary sensor attachment system can also comprise a voltmeter and/or a microprocessor in some embodiments. The voltmeter and/or microprocessor can be coupled to the sensors and to the power supply, and can communicate determined angle data, e.g., wirelessly, to a display device. The system can also store data corresponding to determined angles in a database or other data storage tool. For example, the data can be stored in internal memory or memory coupled to the processor, and/or data can be transmitted to a remote database for storage.

A temporary sensor attachment system can include any number of sensors, such as one, two, three, four, or more. In some embodiments, the different sensors can be configured to be positioned about 90° apart from each other when attached to the prosthetic. For example, one sensor can be positioned along the X axis and a second sensor can be positioned along the Y axis. In embodiments with three sensors, two sensors can be positioned along either of the X or Y axes, and the third sensor can be positioned along the other axis. In other embodiments with three sensors, the three sensors can be arrays at any circumferential positions around the prosthetic, such as at 120° apart from each other. In embodiments with four sensors, two sensors can be positioned along the X axis and two sensors can be positioned along the Y axis, all spaced about 90° apart around the prosthesis (e.g., one in front, one in back, one on medial side, and one on lateral side). Various other configurations can also be utilized in alternative embodiments.

In alternative embodiments, the device can include Bluetooth compatible components and/or other wireless technologies to provide a display of the alignment angles on a user's handheld device or other remote location. The processor can be configured to transmit data corresponding to the determined angles to a remote location, such as another computing device or a data storage device.

When used at a prosthetic ankle joint, for example, one or more of the magnetic intensity sensors can be positioned and used to measure plantar flexion and dorsal flexion angles, and one or more of the sensors can be used to measure supination and pronation angles.

In some embodiments, the sensors are positioned at about the same longitudinal level with the magnet, while in other embodiments the sensors are positioned above the level of the magnet (as illustrated in the attached Figures). The magnet can be positioned anywhere above (e.g., directly above) the pivot point of the prosthetic joint, and/or below the pivot joint.

The disclosed systems can be capable of producing angle readings that are very accurate, such as within 0.5°, within 0.2°, within 0.10, within 0.05°, and/or within 0.010. With accurately quantifiable adjustment changes, less time is required for the iterative process of alignment, and/or the iterative process can be replaced by a single continuous analog adjustment process while reading live angle readings until a desired angle set is reached, then setting the screws. This can optimize the process, save time and cost, increase accuracy and confidence, and ultimately improve the health of patients. Additionally, the disclosed technology can enable a prostheses user to accurately and safely adjust their own prostheses without visiting a clinician, which can save time and mitigate risks and self-injury that can occur when self-adjustment is attempted with conventional technology.

Figure 9:
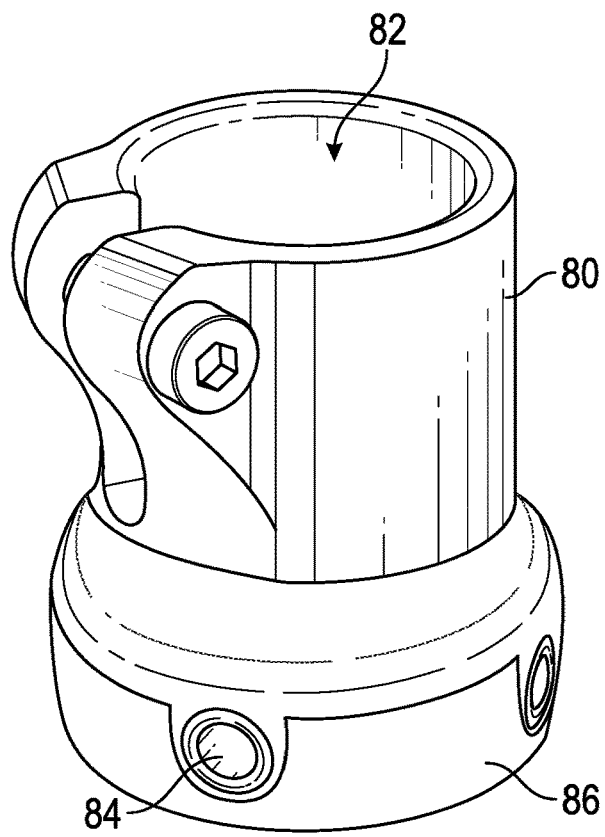
FIG. 9 shows a lower end of an exemplary prosthetic pylon device, including set screws. A smooth outer surface is shown for attaching a sensor system.
Figure 10:
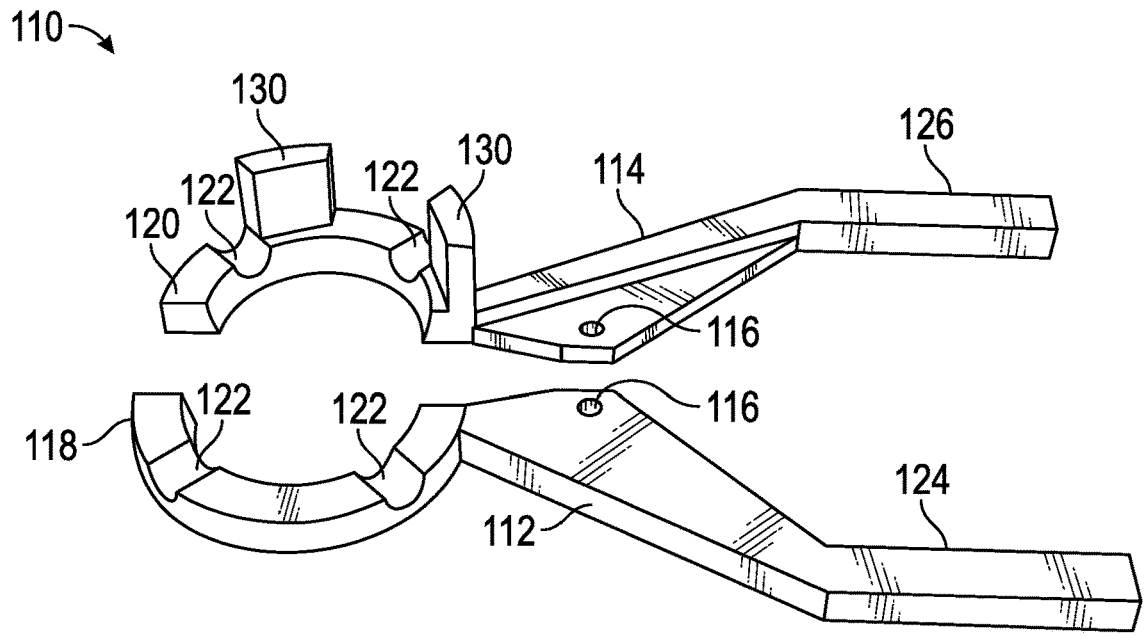
FIG. 10 shows an exemplary clamping device that can carry one or more magnetic intensity sensors and can be temporarily attached to the device of FIG. 9 during the angle setting process, then removed after the angles are fixed.
Figure 11:
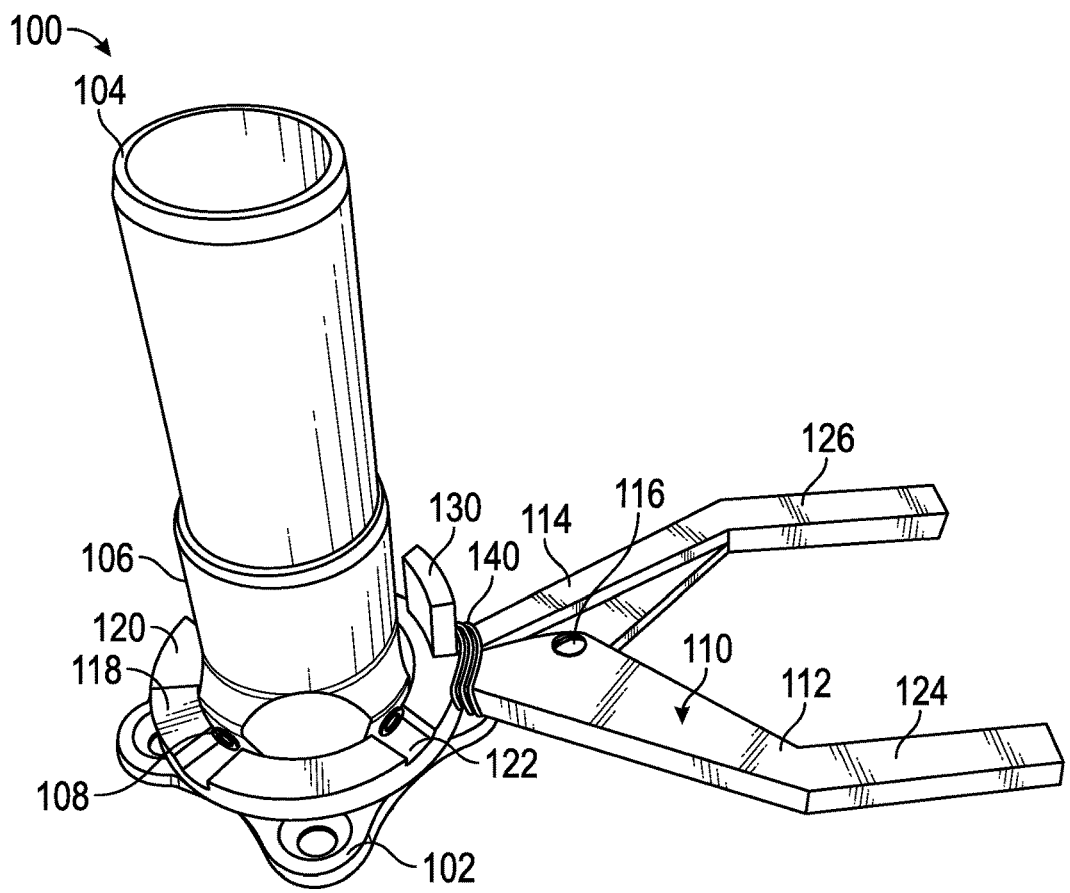
FIG. 11 shows a system including the clamp of FIG. 10 temporarily mounted on a prosthetic joint.

FIGS. 9-11 illustrate an exemplary clamping device 110 that can be used (e.g., instead of a wrap or sleeve) to temporarily position one or more sensors on the prosthetic coupler during the alignment process. It can be beneficial to provide the angle measurement system with a swift attachment and detachment from the prosthesis connector segment whose angle is of interest. For example, a prosthetist may attach the sensor unit to the assembled pyramid adapter/receiver connector, read out the angle data, if necessary change the angle while the sensor is attached and the display continues to show updated data, and detach the sensor system again before the prosthesis user starts walking. In order to not disrupt the established clinical process of angle alignment, the clamp 110 can be used to allow accurate attachment and detachment to be performed, for example by using only one hand and not more than a few seconds.

As shown in FIG. 10, the clamp 110 can comprise a first member 112 and a second member 114 that are pivotably coupled at joint 116. The first member 112 can include an arcuate clamping end 118 and the second member can include a second arcuate clamping end 120 that are configured to be closed around the prosthetic. For example, FIG. 9 shows the lower adapter receiver 80 that couples to a pylon body at upper opening 82. The lower end includes set screws 84 and a circumferential surface 86 between the set screws near the lower end that can receive inner surfaces of the clamping members 118 and 120. As shown in the system 100 of FIG. 11, the members 118, 120 can include notches or openings 122 that align with the set screws 108 of the adaptor receiver 106 to permit adjustment of the screws during the alignment process between the pyramid adapter 102 and the pylon 104.

One or both of the pivoting members 112, 114 can include one or more sensor mounting features 130 to which magnetic intensity sensors can be mounted. As shown, two mounts 130 are included on the clamping member 120, though various other placements can be selected. Sensors can be placed on, in, around, or adjacent to the mounts 130 as desired.

In some embodiments, the clamp 110 can be spring loaded to facilitate automatic closing around the adapter segment. For example, an elastic band 140 is shown in FIG. 11 to bias the clamp to the closed position. In other embodiments, various types of springs or other biasing mechanisms can be included. In an exemplary process, a user can grasp the handles 124, 126 and pull them together to open the clamping members 118, 120 to place the clamp around a prosthetic device. Then, the user can simply release the handles 124, 126 to allow the biasing device to close the clamping members around the prosthetic. This allows for simple, one-handed application and provides clamping force even after the user releases the clamp 110. The opposite can be performed to remove the clamp after the desired angles are achieved.

The area of the clamp 110 that is in contact with the prosthesis can be shaped so that it encompasses a majority of the outer structure of the adapter receiver, the shape of which can be the same or similar across different prosthetic parts (pylons, socket adapters, componentry attachments). The clamp's dimensions can prevent it from interfering with the regular use of the adapter, e.g., there are openings for the set screws that may protrude from the outer surface of the receiver structure and there is nothing that extends beyond the typical build height of such receiver units. By conforming closely to the shape of the structure to which it is attached, the clamp allows consistent placement in an intuitive manner. For example, the clamp device can find its proper position when the biasing member is released and the openings in the clamp are lined up with the set screws.

The disclosed technology can also be utilized at other anatomical locations and with other types of prosthetic couplers. For example, the disclosed technology can be used to determine alignment angles in a prosthetic knee joint, hip joint, or any other lower limb joint. The disclosed technology can also be used to determine angles in a prosthetic joint for other parts of the body, such as for the arms, shoulders, hands, fingers, feet, and/or toes.

Based on the results from both the magnetic field testing and linear lathe testing described herein, devices utilizing the described technology can provide users with the ability to adjust pyramid adaptors' bi-planar alignment angles by displaying two clearly defined X and Y angles. Potential users of this device include prosthetic care providers as well as those who work in prosthetics and orthotics research fields. The disclosed systems can also help mitigate the damage done by self-adjustments from untrained prostheses users.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Integers, characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically, chemically, electrically, magnetically, or otherwise coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. The scope of the disclosure is at least as broad as the following claims.

The invention claimed is:

1. A system for determining alignment angles for prosthetic components, the system comprising:
    a first prosthetic component and a second prosthetic component that are joinable together in a fixed orientation relative to each other, wherein the fixed orientation includes a first angle and a second angle that are perpendicular to each other, and wherein the first and second angles are selectable from a range of angles to provide a desired fixed orientation between the first and second prosthetic components;

a magnet fixedly coupled to the first prosthetic component;

one or more magnetic intensity sensors configured to be coupled to the second prosthetic component in a fixed orientation relative to the second prosthetic component such that the one or more magnetic intensity sensors are operable to sense a magnetic field strength of the magnet and produce an output signal corresponding to the sensed magnetic field strength; and a processor operable to receive the output signal from the one or more magnetic intensity sensors and determine the first angle, the second angle, or both the first and second angles, based on the received output signals from the one or more magnetic intensity sensors and the positions of the one or more magnetic intensity sensors relative to the magnet.

2. The system of claim 1, wherein the one or more magnetic intensity sensors comprise at least two magnetic intensity sensors.

3. The system of claim 1, wherein the one or more magnetic intensity sensors comprise at least one Hall effect sensor.

4. The system of claim 1, wherein the one or more magnetic intensity sensors comprise at least one magnetometer.

5. The system of claim 1, wherein the system further comprises at least one accelerometer configured to sense a position or motion or acceleration of the second prosthetic component and output a corresponding signal to the processor.

6. The system of claim 1, wherein the system includes a removable sleeve or wrap or clamp that includes the one or more magnetic intensity sensors, and the sleeve or wrap or clamp is configured to be secured around the second prosthetic component temporarily to determine the orientation between the two prosthetic components.

7. The system of claim 6, wherein the sleeve or wrap or clamp also includes the processor.

8. The system of claim 6, wherein the sleeve or wrap or clamp also includes a voltmeter operable to measure an output voltage from the one or more magnetic intensity sensors.

9. The system of claim 6, wherein the sleeve or wrap or clamp comprises a clamp, and the clamp is resiliently biased toward a closed position, and is manually opened by actuating a handle and allowed to close by releasing the handle.

10. The system of claim 9, wherein the clamp comprises one or more sensor mounts that are configured to hold the one or more magnetic intensity sensors in desired position relative to the second prosthetic component.

11. The system of claim 1, further comprising a display coupled to the processor, the display operable to display the determined first and second angles.

12. The system of claim 1, wherein the first prosthetic component includes a pyramid adapter and the magnet is fixed to the pyramid adapter, or is a part of the pyramid adapter.

13. The system of claim 1, wherein the first and second prosthetic components are lower limb prosthetic components.

14. The system of claim 1, wherein the magnet is a spherical magnet.

15. The system of claim 1, wherein the processor is configured to transmit data corresponding to the determined angles to a remote computing device or data storage device.

16. A method comprising:

coupling one or more magnetic intensity sensors to a first prosthetic component in a fixed orientation relative to the first prosthetic component, the first prosthetic component being adjustably coupled to a second prosthetic component that includes a magnet fixed relative to the second prosthetic component; and ascertaining at least one angle between the first and second prosthetic components using the one or more magnetic intensity sensors and a processing system coupled to the one or more magnetic intensity sensors, the processing system determining the at least one angle based on output signals from the one or more magnetic intensity sensors, the output signals corresponding to sensed magnetic field strength of the magnet;

wherein coupling the one or more magnetic intensity sensors to the first prosthetic component comprises coupling a clamp to the first prosthetic component, the clamp carrying the one or more magnetic intensity sensors.

17. The method of claim 16, wherein coupling a clamp to the first prosthetic component comprises manually actuating the clamp to open the clamp and then manually releasing the clamp to allow the clamp to close onto the first prosthetic device via a biasing mechanism of the clamp.

* * * * *